United States Patent [19]
Troxler et al.

[11] Patent Number: 6,054,323
[45] Date of Patent: Apr. 25, 2000

[54] METHOD AND APPARATUS FOR ANALYZING ASPHALT CONTENT

[75] Inventors: Robert Ernest Troxler, Raleigh; W. Linus Dep, Chapel Hill; William Finch Troxler, Sr., Raleigh, all of N.C.

[73] Assignee: Troxler Electronics Laboratories, Inc., Research Triangle Park, N.C.

[21] Appl. No.: 09/096,956

[22] Filed: Jun. 12, 1998

[51] Int. Cl.[7] .................................................. G01N 31/12
[52] U.S. Cl. .......................... 436/155; 110/236; 110/345; 422/78; 436/60; 436/139; 436/145; 436/157; 436/160; 436/174; 436/181
[58] Field of Search .............................. 436/60, 139, 140, 436/141, 142, 143, 145, 155, 157, 160, 174, 181; 422/78, 99; 110/185, 190, 236, 345

[56] References Cited

U.S. PATENT DOCUMENTS

| | | | |
|---|---|---|---|
| 2,010,460 | 8/1935 | McKinley | 110/250 |
| 2,705,310 | 3/1955 | Hodge | 439/612 |
| 2,798,928 | 7/1957 | Friedberg | 219/267 |
| 2,855,494 | 10/1958 | Kuebler | 110/210 |
| 4,028,527 | 6/1977 | Thagard, Jr. . | |
| 4,164,655 | 8/1979 | Noma et al. . | |
| 4,347,016 | 8/1982 | Sindelar et al. . | |
| 4,874,950 | 10/1989 | Regimand . | |
| 5,081,046 | 1/1992 | Schneider et al. | 436/139 |
| 5,148,799 | 9/1992 | St-Louis et al. | 126/271.2 |
| 5,151,601 | 9/1992 | Regimand . | |
| 5,558,029 | 9/1996 | Peake . | |

FOREIGN PATENT DOCUMENTS 702578  1/1954  United Kingdom .

OTHER PUBLICATIONS

L. Drüschner *Bitumen* 1993, 55, 158–162.

Todres and Bhattacharja, Solvent–Free, Nuclear–Free Determination of Asphalt Content and Gradation of Hot–Mix Asphalt Concrete; *The American Society for Testing and Materials* (Nov. 1994), pp. 568–574.

Brown, et al., Historical Development of Asphalt Content Determination by the Ignition Method, Journal of the Association of Asphalt Paving Technologist From the Proceedings of the Technical Sessions, vol. 64, (Mar. 27–29, 1995), pp. 241–277.

*Primary Examiner*—Arlen Soderquist
*Attorney, Agent, or Firm*—Alston & Bird, LLP

[57] ABSTRACT

An apparatus and method for assaying an asphalt-containing composite material by irradiating the sample using a radiation source having a tunable preselected wavelength selected to closely approximate the absorbance wavelength of a particular material or materials found in the composite material to reduce the overall time and temperatures ordinarily needed to combust and assay such samples.

27 Claims, 2 Drawing Sheets

METHOD AND APPARATUS FOR ANALYZING ASPHALT CONTENT

FIELD OF INVENTION

The present invention relates to a method and apparatus for testing materials, and more particularly, to a method and apparatus and for processing and testing asphalt-containing composite materials, such as bituminous paving mix used for producing asphalt concrete.

BACKGROUND OF THE INVENTION

Asphalt concrete is a useful material in the road construction industry. Federal and state guidelines require that asphalt concrete laid at certain thicknesses must have certain properties that evidence its safety and long-term performance. If these guidelines are not met, the roadway surface will fail over time when exposed to severe conditions of heat, cold, and moisture. Therefore, samples of asphalt concrete roadway material must be tested to determine proper composition and properties.

When employing composite materials, for example, a bituminous paving mixture, it is generally desirable to test the composition of the materials before installation to ensure that the installed material has desired properties of structural strength, durability, etc. For example, the "hot-mix" asphalt concrete used to pave roads, airport runways, etc., desirably has a predetermined proportion of asphalt binder to aggregate, and a predetermined gradation of aggregate size to help ensure that the material will have adequate and uniform application and wear properties.

Pyrolysis techniques which provide for both content and gradation analyses are known whereby the asphalt binder in a sample of asphalt is burned off to leave an aggregate residue. Pyrolysis techniques are generally described in "Historical Development of Asphalt Content Determination by the Ignition Method," by Brown et al., and in "Solvent-Free, Nuclear-Free Determination of Asphalt Content and Gradation of Hot-Mix Asphalt Concrete," by Todres et al., ASTM Journal of Testing and Evaluation, November 1994, 564–570.

According to these techniques, a sample of asphalt concrete is heated to volatilize and combust the asphalt binder, thus separating the binder from the sample and leaving an aggregate residue. However, insufficient temperatures may not completely separate the binder. Excessive temperatures can lead to aggregate loss and gradation changes induced by chemical changes and thermal shock in the aggregate. Several furnace-type apparatuses have been developed for performing asphalt pyrolysis, including furnaces which incorporate an integral weighing scale in order to allow measurement of a sample of asphalt concrete during pyrolysis as described in, for example, U.S. Pat. No. 5,081,046 to Schneider et al.

Variations in characteristics at installation sites also may lead to variation in combustion conditions. For example, a specimen of hot-mix asphalt may be divided into several samples which may be processed in different furnaces, even different furnaces at different testing sites. Variable combustion conditions in any of the furnaces may lead to inaccurate or nonuniform results among the furnaces. Moreover, non-optimal combustion may lead to deleterious side effects such as poor emissions quality, formation of soot deposits in the furnace and exhaust system, and gaseous discharges into the testing site which may be harmful to personnel and equipment. Afterburners and filters may trap or burn some pollutants which otherwise might be discharged, but still may not produce the combustion and exhaust characteristics to the levels needed to reduce unwanted emissions.

Under currently practiced protocols, hot asphalt concrete samples are placed in stainless steel trays and positioned within a furnace that is pre-heated to an elevated temperature, typically in excess of 500° C. Inside the furnace, the sample is heated by conductive and convective heat transfer to achieve ignition. Heating the sample to the ignition temperature and thereafter combusting the asphalt binder content can require several hours or longer. Weight loss is measured during combustion by an internal balance incorporated in the furnace floor, and final asphalt content is determined.

It has now been discovered that these processes may be inherently inaccurate due to such factors as incomplete combustion, mineral loss, and aggregate gradation changes. For example, furnace temperatures may reach levels for periods of time that cause decomposition of some of the aggregate as well as the binder. In particular, extensive heating can cause cracking and decomposition of the aggregate, resulting in loss of aggregate from the sample and reduction of the aggregate particle size, adversely affecting the accuracy of the overall assay.

SUMMARY OF THE INVENTION

The present invention utilizes radiation heat transfer for pyrolyzing samples of a bituminous paving mix in order to ascertain the asphalt binder content. In a more specific aspect, the present invention uses an infrared heater which emits radiation at an infrared wavelength which heats the asphalt binder in the sample by radiation heat transfer and rapidly elevates the binder to its flash point temperature, at which it ignites. As the infrared heater continues to heat the ignited binder, the asphalt binder present in the sample is combusted. In addition, effluent gases discharged from the binder are also combusted.

The molecular structure of typical asphalt binder shows two infrared (IR) absorption bands at 3.4 $\mu$m and 7.0 $\mu$m. However, typical minerals in aggregate are less absorbent to infrared radiation with wavelengths of from 2 $\mu$m to 7 $\mu$m. For example, quartz, olivine, and orthoclase have absorption peaks at 9 $\mu$m. By irradiating the sample with radiation having wavelengths within the infrared spectrum, energy can be more efficiently transferred directly to the asphalt binder with less heating of the surrounding aggregate. The IR radiation is preferably emitted at wavelengths of from about 2 $\mu$m to about 7 $\mu$m, more preferably from about 2 $\mu$m to about 4 $\mu$m, to closely approximate the absorption bands of the asphalt binder. Hence, the selective heating of the binder results in minimized mineral loss and thermal degradation of the surrounding aggregate, as well as much faster ignition and combustion times.

According to one embodiment of the present invention, a method is provided for assaying the asphalt content of a bituminous paving mix. The method comprises the steps of:

placing a sample of a bituminous paving mix containing aggregate and a combustible asphalt binder in a sample container;

placing the sample container with the sample of bituminous paving mix in a combustion chamber;

exposing the sample to radiation from an infrared heater which emits radiation at an infrared wavelength;

heating the asphalt binder in said sample by radiation heat transfer from said infrared heater until said binder reaches its flash point temperature and ignites; and continuing to heat the ignited binder in said sample by radiation heat transfer from said infrared heater while combusting the asphalt binder present in said sample and effluent gases discharged therefrom.

According to a further embodiment of the invention, an apparatus is provided for pyrolysis of a bituminous paving mix containing aggregate and a combustible asphalt binder. The apparatus comprises:

an oven having a floor, a top wall, and side walls defining a combustion chamber;

a sample support provided within said combustion chamber for receiving and supporting a sample of the paving mix;

an air inlet for admitting air into the combustion chamber;

an outlet for discharging combustion gases from the combustion chamber; and a radiation source mounted within said oven, said radiation source being constructed and arranged for emitting radiation at an infrared wavelength toward said sample holder so as to heat the sample of paving mix by means of radiation heat transfer.

BRIEF DESCRIPTION OF THE DRAWINGS

While some of the objects and advantages of the present invention having been stated, others will be more fully understood from the detailed description that follows and by reference to the accompanying drawings in which.

DETAILED DESCRIPTION OF THE INVENTION

Figure 1:
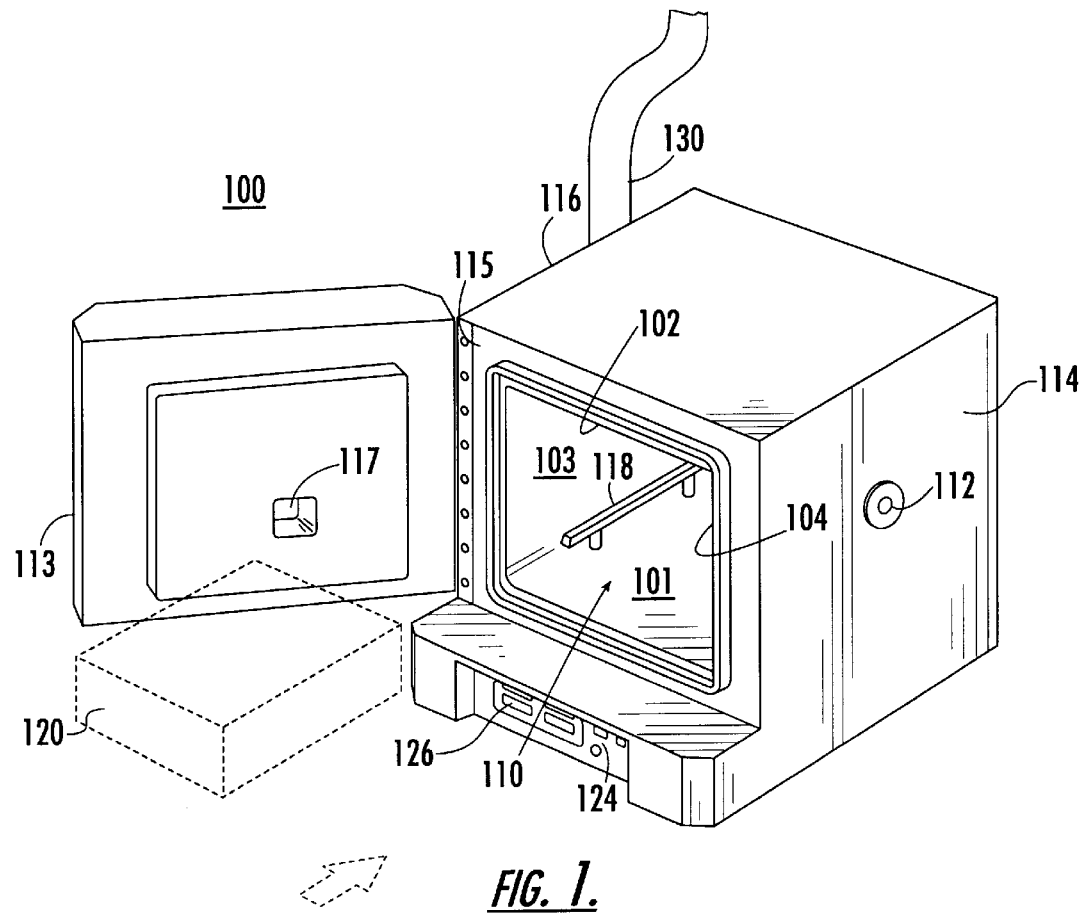
FIG. 1 is a perspective view illustrating a preferred embodiment of an apparatus for analyzing composite materials according to the present invention.

The present invention now will be described more fully hereinafter with reference to the accompanying drawings, in which a specific embodiment of the invention is shown. This invention may, however, be embodied in many different forms and should not be construed as being limited to the embodiments set forth herein. This illustrated embodiment is provided so that this disclosure will be thorough and complete, and will fully convey the scope of the invention to those skilled in the art. In the drawings, the thickness of layers and regions are exaggerated for clarity, and like numbers refer to like elements throughout.

Figure 2:
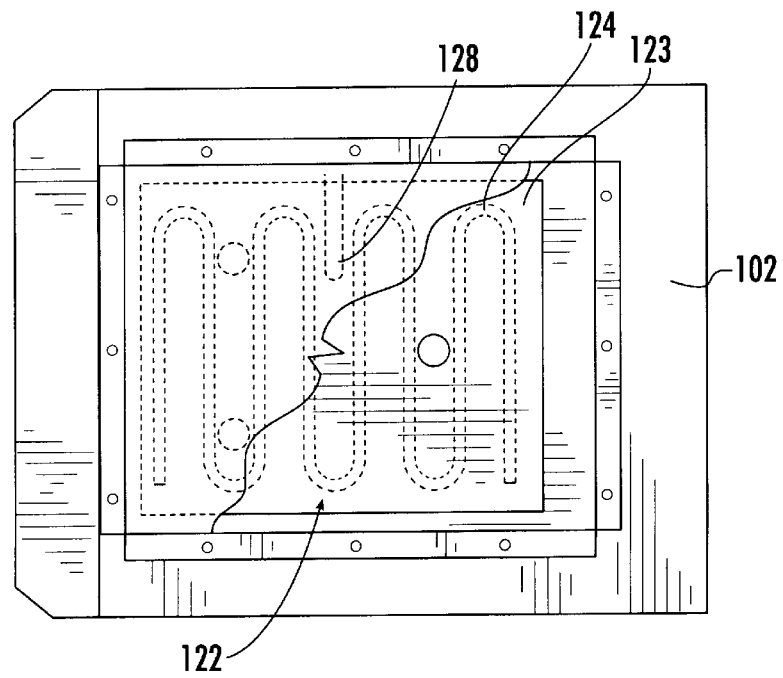
FIG. 2 is a view of the IR radiation source embedded in the top wall of the oven chamber of the apparatus.
Figure 3:
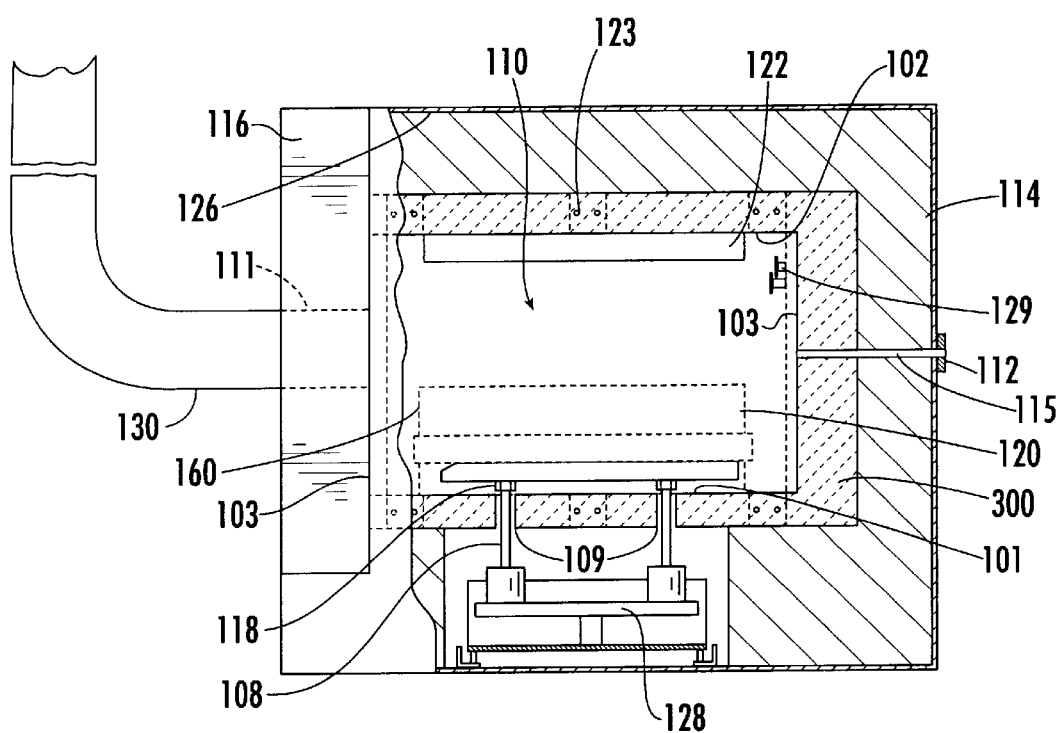
FIG. 3 is a cross-sectional front view of the apparatus of FIG. 1.

FIGS. 1–3 illustrate one embodiment of an apparatus for analyzing and assaying asphalt-containing composite materials, e.g., asphalt concrete, roofing materials and the like, according to the present invention. As shown in FIG. 1, the apparatus includes an oven 100 having a floor 101, a top wall 102, opposing side walls 103, and a rear wall 104 which collectively define a combustion chamber 110. A door 113 is mounted to one of the side walls 103 by a hinge 115 for providing access to the combustion chamber 110. A window 117 in the door 113 allows viewing into the combustion chamber 110 when the door is closed. In the embodiment illustrated in FIGS. 1 to 3, the oven walls 101, 102, 103, 104, and door 113 are provided with a lining 300 of a refractory insulation material. However, the oven chamber may use other forms of insulation besides a refractory material, and may be lined by steel or other materials which are reflective to IR radiation so as to enhance the effect of the IR radiation by redirecting the radiation to the sample. It is further contemplated in a simplified embodiment, that no insulation or minimal insulation is required.

Provided within the chamber 110 adjacent the floor is a sample support adapted for receiving and supporting a sample pan 120 containing a sample of the paving mix. In the embodiment illustrated, the sample support comprises a pair of support rails 118. However, the sample support may take other forms, such as a flat panel or sheet. The support rails 118 are positioned above the floor 101 of the chamber 110 atop a plurality of posts 108 which pass through openings 109 in the floor 101, with the openings 101 preferably having a larger diameter than the posts 108 to allow air to enter the chamber around the posts 108. The lower ends of posts 108 are in turn supported by a weighing device, preferably a load cell 128 beneath the floor 101 of the combustion chamber 110. In this manner, a sample placed within the chamber 110 may be continuously weighed during the pyrolysis procedure.

An infrared heater 122 is mounted within the combustion chamber 110 adjacent the top wall 102 for emitting infrared radiation downwardly toward the sample contained in sample pan 120. The infrared heater includes a block 123 of a refractory material of high heat capacity which is heated by a heating element 124 to a high temperature such that the block radiates energy in the infrared spectrum. Any infrared heater capable of emitting radiation at a predetermined wavelength may be suitably employed. The heating element 124 for the infrared heater may be of the gas fired type or may comprise resistance electric heating elements. One suitable commercially available IR heater is the Casso-Solar type FHT infrared heater available from Casso-Solar Corp., Pomona, N.Y. According to the present invention, the infrared heater is operated at a temperature such that infrared radiation is emitted mostly in the wavelength range of from about 2 to about 7 um. This corresponds to the infrared absorption bands found in typical asphalt binder, and is outside of the range where most aggregate materials have their absorption spectra. For the specific infrared heater noted above, infrared energy of the desired wavelength spectra is emitted when the infrared heater block 123 is heated to a temperature of about 1000 degrees Celsius.

The temperature of the IR heater block 123 is monitored by a suitable temperature sensor 128, such as a thermocouple or thermistor, embedded in the block 123.

The temperature sensor is connected to a temperature controller 124, which controls operation of the heating element 123 to maintain a desired set point temperature. The heater block temperature and the set point temperature are displayed by a digital readout display 126 on the front panel of the oven. An additional temperature sensor 129 may be optionally provided within the combustion chamber for monitoring the chamber temperature.

In the embodiment illustrated, an exhaust outlet opening 111 is provided in a side wall 103 of the oven for discharge of combustion gases produced by pyrolysis of a sample of composite material. Exhaust pipes or ducts 130 may be directly connected to the exhaust outlet opening to carry the combustion gases directly into the atmosphere or into additional pollution treatment devices, or laboratory hoods or similar ventilation apparatus to which the outlet may be connected. Unlike the heavy black combustion gases which are produced when burning a sample in a conventional convection oven, the combustion gases produced from the infrared oven of the present invention are much cleaner, and if desired, may be released directly to the atmosphere without requiring filtration or afterburning. The infrared radiation is believed to be scattered by airborne smoke particles, increasing the efficiency of the oxidization of the smoke particles. However, an afterburner and/or filters optionally may be provided to further combust and/or trap airborne byproducts prior to their release into the atmosphere.

The oven may also be provided with an additional air inlet, preferably on the side wall 104 opposite the side wall where the outlet opening is provided. This air inlet may be provided with an adjustable air flow regulator 112 which can be adjusted to compensate for variations in the exhaust configuration characteristics of the particular installation. Those skilled in the art will appreciate that other embodiments of an adjustable airflow regulator may be used with the present invention. For example, the air intake control or regulator may be any type, but is preferably a rotatable or sliding shutter mechanism. A blower optionally may be included and may include an electrically-powered fan which may be controlled, for example, by a variable speed control which varies the speed of the fan to vary the output of the blower. The adjustable airflow regulator may also include, for example, a restrictable opening such as a mechanically or electromechanically actuated damper or similar device installed at the exhaust outlet housing, in portions of the exhaust system connected thereto, or at the holes in the floor of the oven chamber, which may be adjusted to vary the negative pressure produced by the blower and thus vary the rate at which gases are exhausted from the oven.

The sample pan or tray 120 may be made from any non-reactive material able to withstand repeated heating and cooling cycles. The preferred tray must have sufficient perforations to allow radiation to reach the sample from multiple directions. However, the tray material perforations must be small enough to retain composite material, such as aggregates which are left behind following the liberation of the asphalt from the sample. A wire mesh, or metal screen made from steel or stainless steel able to withstand temperatures in excess of 1200° to 1500° C. are particularly preferred. Other non-metal materials such as ceramics or other refractory materials may be used to make the trays.

Conventional furnace trays have a perforated stainless steel lid to reduce the loss of fine aggregates from the tray system during ignition. It was determined that the preferred trays for use with the apparatus of the present invention require no lid in order to provide maximum IR radiation transfer to the samples. However, the use of quartz or ceramic lids (highly transparent to infrared radiation) are also contemplated by the present invention.

In one embodiment of the present invention, the IR heater source is gas powered. Using such a heater would require only a small amount of electrical power for the controls, and optionally a blower fan. It is therefore contemplated that the gas fired infrared oven of the present invention could be electrically powered with a small battery thus making the unit portable and deliverable to work and testing sites. This would obviate the testing delay resulting from sending samples to testing facilities having ovens located remotely from the site where the asphalt composite is being made and applied.

The furnace of the present invention requires a shorter initial warm-up time than a conventional convection or conduction furnace, since it is only necessary to raise the infrared radiator block 123 to operating temperature, and it is not necessary that the entire combustion chamber be preheated to an elevated temperature. In fact, the operating temperature of the combustion chamber is considerably lower than that of a convection furnace. The IR furnace takes about 15 minutes to warm up whereas a conventional furnace needs a 1 to 3 hour warm up period. In addition, the use of the IR heater facilitates a shorter sample burn time. The IR furnace takes about 30–40 minutes to complete combustion whereas a conventional furnace needs at least 1 hour. Since the infrared radiation from the heater heats only the sample, and not the air in the combustion chamber, the overall temperature of the combustion chamber is much lower. The air is heated only by the combustion itself and by the heat of the sample.

In addition, it is further contemplated that no preheating time may be required, and that sample may be admitted to the IR furnace prior to activating the IR heater. The ignition and combustion times in this "cold start" mode will still be much faster than those obtained using convection-type furnaces.

Having a lower chamber temperature provides significant advantages. When a cold sample pan is first introduced into an oven, temperature differences between the relatively cold sample and its pan and the surrounding environment set up air currents. Because of the necessarily high operating temperature of a conventional convection oven, and resulting large temperature differences, significant air currents are created in the vicinity of the sample pan, which introduce weight measurement errors when attempting to measure the initial weight of the sample. The temperature differences are much lower in the furnace of the present invention, and the resulting air currents have minimal error introducing effect. Further, since the aggregates present in the sample are heated to lower temperatures and for shorter periods of time, changes to or losses in the aggregate as a result of charring, spalling or explosion are minimized. The use of the IR furnace therefore minimizes mineral losses and thermal degradation (alteration) of the aggregate. The minimized heating facilitated by the apparatus and methods of the present invention further minimize the risk of loss of minerals through calcination and also lowers the rate of carbonate dissociation; all of which affects weight measurement accuracy.

Still further, a lower chamber temperature is desirable to decrease the effect of temperature "plunge" as the oven door is opened to admit the sample trays. In convection ovens, opening of the furnace door realized a temperature drop on the order of 100° C. or more, which increased the reheating cycle time. The combustion chamber temperature in the furnaces of the present invention typically do not exceed about 300° C. during operating when empty, and only sustain a plunge of about 25° C. as the sample is admitted.

Overall, the chamber temperature is not critical with the present invention since the radiation is targeted specifically to the asphalt component of the composite sample. The asphalt is irradiated with IR radiation and heats up much more quickly, thus liberating byproduct gases from the asphalt which are then ignited in the furnace at much lower temperatures. The flash point of the asphalt gases is about 315° C. This is the highest temperature required by the furnaces of the present invention. Once the gas ignites, the sample will burn and the reaction temperature will rise in excess of 500° C.

In addition, since the overall internal chamber temperatures of the present invention are lower, infrared furnaces may not need thick refractory walls. This will provide a smaller, lighter structure, and economize manufacturing. This is important in allowing for the design of a portable structure that can be used on site.

The following example serves only to further illustrate aspects of the present invention and should not be construed as limiting the invention.

EXAMPLE 1

Combustion of Asphalt-Containing Composite Samples

Two stainless steel sample trays (2.125"×9"×13") were used to contain and orient the asphalt concrete. The tray had perforations having a 0.125" hole size with 0.1875" hole spacing. This perforation provided transmission to infrared radiation, with the stainless steel acting as a reflector for infrared radiation such that a sufficient amount of infrared radiation penetrated the perforated bottom of the top tray and heated the sample in the bottom tray. The perforations also provided adequate air circulation necessary for asphalt binder ignition and provided for a more complete asphalt burn. The sample trays were not covered in order to provide a more complete transfer of infrared heat from the infrared source to the sample on the top tray. A polished stainless steel flat plate was placed on a regular catch pan. Metal spacers of about 0.25" height were placed on the flat plate. On the spacers, were placed the two trays. The flat metal plate functions as act as a reflector for infrared and confine the radiation in the sample volume and keeps any fall-out of asphalt coated grains of aggregate near the bottom of the second pan. When the asphalt cement in the second pan ignited, the flames move towards the flat plate and ignite grains on the plate. The spacers provide good air circulation through the sample for quicker ignition and a more even and complete burn.

After powering up the infrared heaters, it took about 15 minutes to heat the infrared panel to 975° C. The chamber temperature was 185° C. The tray system was weighed using an external balance. A sample of 1000 g of hot asphalt on each sample tray (CC Magnum asphalt concrete with about 6.5% asphalt content, total sample weight about 2000 g). The sample was weighed in the tray system using an external balance. The tray system was then placed in the furnace. In less than 2 minutes, the asphalt in the top tray ignited, and the process continued igniting asphalt layer-by-layer downward. Within about 6–8 minutes, the asphalt in the bottom pan ignited. The chamber temperature reached a maximum of about 230° C. within 10 minutes after placing the sample into the furnace. When the burn was over, the sample tray system was removed from the furnace and allowed to cool down in open air. The total weight of the tray system was measured using the external balance.

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. In the drawings and specification, there have been disclosed typical embodiments of the invention and, although specific terms are employed, they are used in a generic and descriptive sense only and not for purposes of limitation, the scope of the invention being set forth in the following claims.

That which is claimed:

1. In a method for assaying the asphalt content of a bituminous paving mix wherein a sample of s bituminous paving mix containing aggregate and a combustible asphalt binder is heated, the combustible asphalt binder is combusted, and the weight loss resulting from combustion of the asphalt binder is measured to determine the amount of asphalt binder originally present in the sample, the improvement which comprises directing radiation into the sample from an infrared heater which emits radiation at an infrared wavelength and heating the asphalt binder in said sample by radiation heat transfer from said infrared heater until said binder reaches its flash point temperature and ignites, and continuing to heat the ignited binder in said sample by radiation heat transfer from said infrared heater while combusting the asphalt binder present in said sample and effluent gases discharged therefrom.

2. A method according to claim 1, wherein said infrared heater is operated at a wavelength of about 2 to about 7 micrometers.

3. A method according to claim 1, wherein said infrared heater is operated at a temperature of about 1000 degrees C.

4. A method for assaying the asphalt content of a bituminous paving mix, said method comprising:

placing a sample of a bituminous paving mix containing aggregate and a combustible asphalt binder in a sample container;

placing the sample container with the sample of bituminous paving mix in a combustion chamber;

exposing the sample to radiation from an infrared heater which emits radiation at an infrared wavelength;

heating the asphalt binder in said sample by radiation heat transfer from said infrared heater until said binder reaches its flash point temperature and ignites; and continuing to heat the ignited binder in said sample by radiation heat transfer from said infrared heater while combusting the asphalt binder present in said sample and effluent gases discharged therefrom.

5. A method according to claim 4, wherein said steps of heating the asphalt binder to its flash point and combusting the asphalt binder are carried out while the air in the combustion chamber surrounding the sample container remains at a temperature below the flash point of the asphalt binder.

6. A method according to claim 4, wherein said heating steps include locating the infrared heater in said combustion chamber above the sample container and oriented for radiating infrared radiation downwardly into the sample.

7. A method according to claim 6, including the step of heating the infrared heater with a gas burner.

8. A method according to claim 6, including the step of heating the infrared heater with an electric resistance heating element.

9. A method according to claim 6, additionally includes the steps of admitting airflow into the combustion chamber through an inlet and discharging combusted effluent gases from the combustion chamber through an outlet.

10. A method according to claim 9, additionally including the steps of adjustably restricting the inlet to control air intake into the combustion chamber.

11. A method according to claim 4, including the steps of initially measuring the weight of the sample container and the uncombusted sample and subsequently measuring the weight of the sample container and the combusted sample.

12. A method according to claim 11, wherein said combustion chamber includes a support for receiving the sample container, said support being equipped with a weighing device, and wherein said weight measuring steps are carried out within said combustion chamber by said weighing device.

13. A method according to claim 11, including the further step, performed prior to said step of placing the sample container with the sample in the combustion chamber, of operating said infrared heater with the combustion chamber empty so that the infrared heater preheats the combustion chamber to a temperature not exceeding 500 degrees C.

14. The method according to claim 4, wherein the sample is ignited within about 4 minutes after being introduced into the combustion chamber.

15. The method according to claim 4, wherein said step of placing a sample of a bituminous paving mix containing aggregate and a combustible asphalt binder in a sample container comprises placing the sample in at least one open tray.

16. An apparatus for pyrolysis of a bituminous paving mix containing aggregate and a combustible asphalt binder, said apparatus comprising:

an oven having a floor, a top wall, and side walls defining a combustion chamber;

a sample support provided within said combustion chamber for receiving and supporting a sample of the paving mix;

an air inlet for admitting air into the combustion chamber;

an outlet for discharging combustion gases from the combustion chamber;

an infrared heater mounted within said oven, said heater being constructed and arranged for emitting radiation at an infrared wavelength onto said sample support so as to heat the sample of paving mix to combustion by means of radiation heat transfer;

a sample pan positionable within said combustion chamber on said sample support; and a weighing instrument cooperating with said sample support for detecting changes in the weight of the sample on said sample pan during pyrolysis of the paving mix.

17. The apparatus according to claim 16, wherein said infrared heater is operable at a predetermined wavelength selected to preferentially transfer heat into said combustible bituminous binder.

18. The apparatus according to claim 16, wherein the infrared heater is operable at a predetermined wavelength corresponding to the infrared absorption spectra of said combustible bituminous binder.

19. The apparatus according to claim 18, wherein said infrared heater comprises a block of refractory material and a heater cooperating with said refractory block for heating the block to an elevated temperature at which the block radiates energy in the infrared spectrum.

20. The apparatus according to claim 19, including a temperature sensor mounted in said refractory block, and a temperature controller connected to said heater and responsive to said temperature sensor for maintaining said refractory block at a preselected temperature.

21. The apparatus according to claim 19, wherein said heater is gas operated.

22. The apparatus according to claim 19, wherein said heater is an electrical resistance heating element.

23. The apparatus according to claim 16, further comprising an adjustable airflow regulator in communication with the combustion chamber operable to adjustably control the airflow to provide for substantially complete pyrolysis of airborne pyrolysis byproducts.

24. The apparatus according to claim 23, wherein the infrared heater emits energy at a wavelength spectrum including from about 2 to about 7 micrometers.

25. The apparatus according to claim 12, wherein said sample support comprises spaced apart rails positioned above said floor and arranged for supporting said sample pan.

26. An apparatus for pyrolysis of a bituminous paving mix containing aggregate and a combustible asphalt binder, said apparatus comprising:

an oven having a floor, a top wall, opposing side walls, and a rear wall defining a combustion chamber, and including a door opposite said rear wall for providing access to the combustion chamber;

a sample support provided within said combustion chamber for receiving and supporting a sample pan containing a sample of the paving mix;

a plurality of posts carried by said sample support and extending downwardly therefrom;

a plurality of openings formed in the floor of said oven, said posts extending downwardly through said openings and mounting the sample support in spaced relation above the floor of said oven;

a weighing device positioned beneath said floor external to said oven and being operatively connected to said posts to enable the weighing device to sense the weight of a sample of paving mix in said sample pan;

an outlet opening in said oven for discharging combustion gases from the combustion chamber; and an infrared radiation heater mounted within said combustion chamber adjacent said top wall, said infrared heater including a radiation source arranged for emitting infrared radiation downwardly onto said sample pan at an infrared wavelength to transfer heat into said combustible bituminous binder by means of radiation heat transfer.

27. The apparatus according to claim 26, wherein the weighing device is a load cell.

* * * * *

UNITED STATES PATENT AND TRADEMARK OFFICE
CERTIFICATE OF CORRECTION

PATENT NO. : 6,054,323
DATED : April 25, 2000
INVENTOR(S) : Troxler et al.

It is certified that error appears in the above-identified patent and that said Letters Patent is hereby corrected as shown below:

Title page, [73] Assignee, "Electronics" should read --Electronic--.

Column 7, line 60, before "bituminous" the letter "s" should read --a--.

Column 10, line 11, "claim 12" should read --claim 16--.

Signed and Sealed this

Twenty-seventh Day of February, 2001

Attest:

Attesting Officer

NICHOLAS P. GODICI

Acting Director of the United States Patent and Trademark Office